(12) United States Patent
Harper

(10) Patent No.: US 10,176,696 B2
(45) Date of Patent: Jan. 8, 2019

(54) APPARATUS AND PROCESS FOR MEASURING GASEOUS EMISSIONS FROM AN ENGINE

(71) Applicant: Richard Harper, New Braunfels, TX (US)

(72) Inventor: Richard Harper, New Braunfels, TX (US)

(*) Notice: Subject to any disclaimer, the term of this patent is extended or adjusted under 35 U.S.C. 154(b) by 208 days.

(21) Appl. No.: 14/942,018

(22) Filed: Nov. 16, 2015

(65) Prior Publication Data

US 2016/0146142 A1    May 26, 2016

Related U.S. Application Data

(60) Provisional application No. 62/082,689, filed on Nov. 21, 2014.

(51) Int. Cl.

| | | |
|---|---|---|
| *G08B 21/14* | (2006.01) | |
| *G01N 33/00* | (2006.01) | |
| *G01M 15/10* | (2006.01) | |
| *F02D 19/02* | (2006.01) | |
| *F02D 41/14* | (2006.01) | |
| *F02D 41/02* | (2006.01) | |
| *F02D 41/22* | (2006.01) | |
| *F02D 41/00* | (2006.01) | |

(52) U.S. Cl.
CPC ............ *G08B 21/14* (2013.01); *F02D 19/02* (2013.01); *G01M 15/102* (2013.01); *G01M 15/104* (2013.01); *G01N 33/0036* (2013.01); *F02D 41/0027* (2013.01); *F02D 41/1444* (2013.01); *F02D 2041/228* (2013.01)

(58) Field of Classification Search
CPC ...... G08B 21/14; G01M 15/102; F02D 19/02; F02D 2041/228; F02D 41/0027; F02D 41/1444; G01N 33/0036
See application file for complete search history.

(56) References Cited

U.S. PATENT DOCUMENTS

| | | |
|---|---|---|
| 4,329,870 A | 5/1982 | Farmer |
| 4,567,366 A | 1/1986 | Shinohara |
| 4,591,414 A | 5/1986 | Zaromb et al. |
| 4,871,916 A | 10/1989 | Scott |

(Continued)

FOREIGN PATENT DOCUMENTS

JP        03074550 A  *  3/1991

*Primary Examiner* — Hung Q Nguyen
*Assistant Examiner* — Brian P Monahon
(74) *Attorney, Agent, or Firm* — Egbert Law Offices, PLLC

(57) ABSTRACT

A process for measuring methane emissions by an internal combustion engine includes connecting a methane sensor to an exhaust line of the internal combustion engine such that a portion of the gas in the exhaust line can enter the methane sensor, operating the internal combustion engine so as to produce the exhaust, measuring a methane concentration of the gas from the portion of the gas from the exhaust line with the methane sensor, and producing an output from the methane sensor corresponding to the methane concentration. The methane sensor is plumbed to the exhaust line. The methane concentration is continuously sampled by the methane sensor. The methane sensor can be an electrochemical cell, a catalytic methane sensor, or an infrared methane sensor.

2 Claims, 5 Drawing Sheets

(56) References Cited

U.S. PATENT DOCUMENTS

| | | | |
|---|---|---|---|
| 5,131,224 A | 7/1992 | Siewert et al. | |
| 5,311,851 A * | 5/1994 | Wright, Jr. | F02B 1/02 123/198 D |
| 5,595,163 A * | 1/1997 | Nogi | F02D 41/0027 123/494 |
| 5,614,658 A * | 3/1997 | Moss | F01N 13/008 60/286 |
| 5,767,388 A | 6/1998 | Fleischer et al. | |
| 5,839,274 A * | 11/1998 | Remboski | F01N 11/00 60/274 |
| 5,969,623 A * | 10/1999 | Fleury | G01N 33/004 340/632 |
| 5,993,625 A * | 11/1999 | Inoue | G01N 27/419 204/425 |
| 6,136,170 A * | 10/2000 | Inoue | G01N 27/4065 204/408 |
| 6,153,072 A * | 11/2000 | Inoue | G01N 27/417 204/425 |
| 6,242,263 B1 * | 6/2001 | Faber | F01N 11/00 422/94 |
| 6,308,130 B1 * | 10/2001 | Vojtisek-Lom | G01M 15/10 701/114 |
| 6,344,173 B1 * | 2/2002 | Faber | G01N 27/16 422/94 |
| 8,510,017 B2 * | 8/2013 | Sawada | F02D 41/0085 123/673 |
| 8,788,181 B2 * | 7/2014 | Stuart | G01M 3/002 701/108 |
| 9,677,976 B2 * | 6/2017 | Chrin, II | G01N 1/2247 |
| 2007/0022733 A1 * | 2/2007 | Sako | F02C 3/22 60/39.12 |
| 2007/0220955 A1 * | 9/2007 | Noda | G01M 15/102 73/31.05 |
| 2007/0254196 A1 * | 11/2007 | Richards | F01D 15/10 60/39.281 |
| 2008/0011248 A1 * | 1/2008 | Cutlip | E21F 7/00 123/3 |
| 2010/0083635 A1 * | 4/2010 | Kitaura | F01N 3/10 60/276 |
| 2010/0115840 A1 * | 5/2010 | Shito | B01D 53/0476 48/127.9 |
| 2010/0196833 A1 * | 8/2010 | Seki | C01B 3/384 431/2 |
| 2011/0303200 A1 * | 12/2011 | Zeitoun | F02M 35/12 123/568.11 |
| 2012/0206715 A1 * | 8/2012 | Laub | G01N 33/0047 356/51 |
| 2012/0239279 A1 * | 9/2012 | Stuart | F02D 19/0623 701/107 |
| 2012/0239308 A1 * | 9/2012 | Miller | G01N 21/3504 702/24 |
| 2013/0042599 A1 * | 2/2013 | Shinoda | F01N 3/2073 60/285 |
| 2013/0067913 A1 * | 3/2013 | Nishio | F02M 33/04 60/599 |
| 2013/0158757 A1 * | 6/2013 | Han | H01M 8/04664 701/22 |
| 2013/0192203 A1 * | 8/2013 | Zemskova | F01N 3/106 60/274 |
| 2013/0276431 A1 * | 10/2013 | Aoki | G01N 27/407 60/276 |
| 2014/0069384 A1 * | 3/2014 | Suzuki | F02D 41/403 123/445 |
| 2014/0208766 A1 * | 7/2014 | Amin | F02C 7/224 60/778 |
| 2014/0250857 A1 * | 9/2014 | Kajita | B01D 53/864 60/39.5 |

\* cited by examiner

APPARATUS AND PROCESS FOR MEASURING GASEOUS EMISSIONS FROM AN ENGINE

RELATED U.S. APPLICATIONS

The present application claims priority from United States Provisional Patent Application Ser. No. 62/082,689, filed on Nov. 21, 2014, and entitled "Apparatus and Process for Measuring Gaseous Emissions from an Engine".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to gas measurement. More particularly, the present invention relates to gas measurement of methane emissions of an internal combustion engine. More particularly, the present invention relates to methane sensors that are utilized so as to provide an indication of excess methane emissions from an internal combustion engine.

2. Description of Related Art Including Information Disclosed Under 37 CFR 1.97 and 37 CFR 1.98.

Although most automobile, truck and industrial engines are operated on gasoline or diesel fuel, natural gas is recognized as a potential fuel for such engines because it is viewed as a "clean" fuel. Natural gas comprises mostly methane ($CH_4$). It has been found that engines operate with methane or natural gas as a fuel produce lower amounts of carbon monoxide, carbon dioxide and unburned hydrocarbons of the type that contribute to smog than engines operated on gasoline. The lower quantity of such hydrocarbon emissions is seen as particularly beneficial because of the corresponding reduction in the formation of ground level ozone. The reduction in carbon dioxide is also beneficial because carbon dioxide is a greenhouse effect gas. Since gasoline and natural gas are both hydrocarbon fuels, it would seem that operating practices and exhaust treatment techniques developed for gasoline engines would be directly applicable to methane-fueled engines. However, such is not the case.

During the past, noble metal catalysts supported on high surface area alumina carriers have been developed to complete the oxidation of carbon monoxide and unburned hydrocarbons in gasoline engine exhaust. Platinum and/or palladium dispersed as very fine particles on pellets or greens of alumina have served as oxidation catalysts. These catalysts have proven most effective when there is an excess of oxygen in the exhaust gas resulting when the engine is operating in a fuel-lean or excess-air mode. The catalytic conversion of nitrogen oxides to nitrogen is a chemical reduction-type reaction which is most favorably carried out in an oxygen-deficient environment than is the antithesis of a favorable oxidation reaction medium. Under suitable engine operating conditions, a three-way catalyst promotes simultaneously the oxidation of carbon monoxide to carbon dioxide, the oxidation of unburned hydrocarbons to carbon dioxide and water and the reduction of nitrogen oxides to nitrogen. The three-way catalyst practice represents the current state of the art in gasoline-fueled engine exhaust treatment. The problem has been discovered with natural gas fueled engines is that when operated with a three-way catalyst in accordance with gasoline-fueled engine practices, unburned methane passes unoxidized through the exhaust system into the atmosphere. Although methane is not poisonous and it is not a reactive hydrocarbon in the sense that it promotes ozone formation at low altitudes, it is a greenhouse effect gas. It remains in the atmosphere and has many times the atmospheric heat-reflecting aspects of carbon dioxide.

Methane is not readily oxidized in an oxygen-rich exhaust gas over the traditional noble metal catalyst. These catalyst do not become "active" to oxidize methane until heated to very high temperatures (i.e. 600° C. or higher) which the exhaust gases usually do not attain. Thus, while the engine emissions with methane fuel are favorable compared to gasoline-fueled engines, there remains the problem of preventing unburned methane from escaping the engine's exhaust system into the atmosphere. Heretofore, there has been little effort in monitoring and controlling the emissions of methane from such natural gas fueled engines.

Methane emissions are monitored by the EPA and the Texas Commission on Environmental Quality ("TCEQ"). Industrial-grade engines that are being used in the oil and gas fields are designed to operate in austere conditions and even continue to operate in the event that multiple cylinders have suffered catastrophic failures. In doing so, there will be a significant increase in the amount of methane present in the engine exhaust. An engine can run continually in conditions such as this and cause the owner or operator to be responsible for the increased emissions and any fine deemed appropriate by the EPA or the TCEQ. As such, a need has developed so as to provide a device that can prevent this type of lost revenue and enhance the technical capabilities of the mechanics and operators.

There has not yet been any attempt to solve the problems associated with excessive methane emissions in industrial natural gas engines because of the lapse in technology and the lack of enforcement of environmental standards. However, in recent years, it has become a high priority and is now monitored regularly by the EPA and the TCEQ.

One of the problems with attempting to sense methane emissions from internal combustion engines is that water vapor is always present in the exhaust stream of a natural-gas fueled engine and rapidly condenses to form droplets as the engine exhaust cools. In any methane sensing system, the results and the detection can be compromised by contact with these water droplets or as a result of excess water within the exhaust gas being sampled. As such, a need has developed so as to provide a methane sensor which effectively avoids the problems associated with water vapor in the exhaust stream.

In the past, various patents have issued relating to the measurement of methane concentrations. For example, U.S. Pat. No. 4,329,870, issued on May 18, 1982 to D. E. Farmer, shows a methane monitor sensing system. This methane monitor has at least one removable and replaceable sensor interchangeably inserted into a receptacle located on the outside wall of the monitor.

U.S. Pat. No. 4,591,414, issued on May 27, 1986 to Zaromb et al., describes a method of determining methane and an electrochemical sensor therefor. An electrochemical cell is used for the detection and measurement of methane in a gas by the oxidation of methane electrochemically at a working electrode and a nonaqueous electrolyte at a voltage of about 1.4 volts versus the reversible hydrogen electrode potential in the same electrolyte. A measurement of the electrical signal resulting from the electrochemical oxidation is obtained.

U.S. Pat. No. 4,567,366, issued on Jan. 28, 1986 to A. Shinohara, discloses a method and apparatus for measuring methane concentration in a gas. This method and apparatus comprises a transmitting light having at least one wavelength band selected from a band of 1.6 µm and a band of 1.3 µm through an optical fiber having a small transmission loss in the wavelength bands to a measuring cell wherein ambient gas comes in and out. Light is absorbed in at least the characteristic absorption wavelength of methane gas. The light is transmitted through an optical fiber having a small transmission loss. The light is separated into at least one light having the methane gas absorption wavelength. At least one light has another reference wavelength so as to allow for the determination of the intensity ratio of the light having the wavelength to be measured to light having the reference wavelength. Methane gas concentration is calculated in the measuring cell from the so-determined intensity ratio.

U.S. Pat. No. 4,871,916, issued on Oct. 3, 1989 the J. C. Scott, teaches the sensing of methane using a spectroscopic method. This spectroscopic method senses the presence of methane in atmosphere. Atmospheric light emitted by a neodymium laser is utilized so as to have a fluorescent linewidth which embraces at least one significant absorption line of the band of methane.

U.S. Pat. No. 5,311,851, issued on May 17, 1994 to H. W. Wright Jr., provides a methane monitor and engine shutdown system. The system is used to detect methane gas at oil well and natural gas well sites. The system generates a warning signal when a first lower concentration of methane gas is detected and generates a second signal when a higher, more dangerous, level of methane gas is detected. The methane monitoring control and sensor device is mounted within the environment of an internal combustion engine and is used to detect the concentration levels of methane gas and generate two signals. A first signal generates a warning and a second signal will effect engine shutdown by means of a compressed air-operated valve closing the air intake to the engine.

U.S. Pat. No. 5,767,388, issued on Jun. 16, 1998 to Fleischer et al., discloses a methane sensor and method for operating such a sensor. The sensor has a temperature in a range of 700° to 850° C. for detecting methane and an oxygen-sensitive semiconducting metal oxide.

U.S. Pat. No. 5,131,224 provides a method for reducing methane exhaust emissions from natural gas fueled engines. This method allows the operating of the engine with an air-fuel ratio within a range that includes the stoichiometric air-fuel ratio and extends to the fuel-rich side. The system employs in combination with the engine a platinum or platinum and palladium metal catalyst for treatment of the engine and exhaust gases.

U.S. Pat. No. 5,969,623, issued on Oct. 19, 1999 to Fleury et al., describes a gas alarm that includes a methane sensor coupled to a processor for independently sensing methane levels such that an alarm is activated when the methane levels are above a predefined threshold.

It is an object of the present invention to provide a methane gas detection system that effectively detects methane concentrations as emitted from an internal combustion engine.

It is another object of the present invention provide a method and apparatus that enhances the technical capability of mechanics and operators.

It is another object of the present invention provide a method and apparatus that provides data to the mechanics and operators.

It is still a further object of the present invention provide a methane detection method and apparatus that helps to avoid fines by government authorities.

It is still another object of the present invention provide a methane detection apparatus and method that prevents lost revenue.

It is still a further object of the present invention provide a method and apparatus for detecting methane emissions that enhances environmental quality.

It is another object of the present invention to provide a methane detection apparatus and method which is extremely durable.

It is another object of the present invention to provide a methane detection apparatus and method that can be of a relatively small size.

It is still another object of the present invention to provide a methane detection apparatus and method that is reliable in the presence of a corrosive gas, such as hydrogen sulfide.

It is still another object of the present invention to provide a methane detection apparatus and method that is extremely accurate and reliable.

It is a further object of the present invention to provide a methane detection apparatus and method which allows the levels of methane to be easily observed.

These and other objects and advantages of the present invention will become apparent from a reading of the attached specification and appended claims.

BRIEF SUMMARY OF THE INVENTION

The present invention is a process for measuring methane emissions by an internal combustion engine. This process includes the steps of: (1) connecting a methane sensor to an exhaust line of the internal combustion engine such that a portion of a gas in the exhaust line can enter the methane sensor; (2) operating the internal combustion engine so as to produce the exhaust; (3) measuring a methane concentration of the gas from the portion of the gas from the exhaust line with the methane sensor; and (4) producing an output from the methane sensor corresponding to the methane concentration.

The step of connecting includes plumbing the methane sensor to the exhaust line. In particular, the exhaust line is connected between an exhaust of the cylinder of the internal combustion engine, and exhaust catalyst and an exhaust silencer (or muffler). The methane sensor is plumbed to the exhaust line in a location beyond the exhaust catalyst. Ideally, the methane sensor is plumbed between the exhaust catalyst and the exhaust silencer.

The step of measuring includes continuously sampling methane concentrations over time. The output from the methane sensor can be passed to a controller. An operation of the internal combustion engine can be controlled by the controller relative to the output from the methane sensor.

The step of producing an output includes transmitting a humanly perceivable signal relative to a level of the methane concentration measured by the methane sensor. This humanly perceivable signal can be an indicator light. Alternatively, this humanly perceivable signal can be an audible alarm.

The methane sensor can be mounted to a platform. This platform can be affixed to a skid of the internal combustion engine.

In one embodiment of the present invention, the methane sensor is connected to the exhaust in a pair of spaced-apart locations. A first portion of the gas is passed from one of the spaced apart locations to the methane sensor. A second portion of the gas from another of the spaced apart locations is also passed to the methane sensor. These two sampling locations are particular useful for engines that have more than one exhaust bank. As such, the methane sensor is able to receive a portion of the exhaust gas from two separate locations along the exhaust lines. The methane sensor is positioned within a housing. The portion of the gas enters the housing prior to measurement by them methane sensor. The housing is connected to the exhaust line of the internal combustion engine. A baffle is formed within the housing in a location such that the portion of the gas encounters the baffle prior to measurement by the methane sensor. Water is separated from the portion of the gas by the baffle prior to being measured by the methane sensor. This water is discharged outwardly from an interior of the housing.

The step of connecting includes extending the line from an inlet of the housing to the exhaust line. The baffle is positioned within the housing adjacent to the inlet of the housing. An outlet is formed in the housing in the location below the baffle at a level below the inlet. The methane sensor is positioned at an upper location within the housing such that only gas flows through the housing to the methane sensor. The methane sensor can be either an electrochemical cell, a catalytic methane sensor, or an infrared methane sensor.

The present invention is also a methane sensing apparatus that comprises a housing having an inlet and an outlet, a methane sensor positioned in the housing at a level above a level of the inlet and above a level of the outlet, and a baffle positioned in the housing adjacent to the inlet and above the outlet and below the methane sensor. The outlet is positioned at a level lower than a level of the inlet. The baffle is adapted to separate water from the gas within the housing. A mounting skid can be affixed to the housing. This mounting skid is adapted to allow the housing to be affixed to an internal combustion engine or to a skid of the internal combustion engine. A line is connected to the inlet and plumbed to an exhaust line of the internal combustion engine. This line passes a portion of the exhaust gas flowing through the exhaust line to an interior of the housing.

The method and apparatus of the present invention provides technical data to mechanics and operators are responsible for the operation and maintenance of industrial natural gas-powered engines. The data that is provided by the method and apparatus of the present invention can be in the form of an alarm or a numerical value that represents the methane concentration in the exhaust of the engine. The device continuously samples the engine exhaust for the amount of methane present in the exhaust stream. By doing so, there will be provided an abundance of information that is available to the mechanic and operator of the equipment. If desired, the device can communicate via CAN or J1939 with the engine controller to provide an alarm input to the engine control panel.

This type of data is valuable in the manner in which the methane emissions are being monitored by the EPA and the TCEQ. The data provided by the present invention prevents lost revenue and enhances the technical capabilities of the mechanics and operators.

The components that are required to make the device work are a methane sensor for identifying the presence of methane, a circuit board to drive the methane sensor and generate a signal output, a housing and an associated wiring harness. The housing and the signal output can easily be modified to fit multiple applications. Most likely, the housing and the signal output can be the size of a cell phone and can incorporate status lights during normal operation.

The system can be adapted for other functions. In particular, the system can be adapted to fit on propane-powered engines or multi-fuel engines. In doing so, a different electrochemical cell would be used in order to establish a threshold for excessive propane or other gases in the engine exhaust. The device is installed in a stationary location on the engine skid. A stainless steel line is plumbed from the engine exhaust pipe to the device on the engine skid. The exhaust sample should come from an area between the catalyst and the exhaust silencer on the engine. This will produce a positive pressure to feed untreated exhaust to the sample line tubing and allow the exhaust sample to flow to the methane sensor without any moving parts.

This foregoing section is intended describe, with particularity, the preferred embodiments of the present invention. It is understood that modifications to these preferred embodiments can be made within the scope of the present claims. As such, the section should not be construed, in any way, as limiting of the broad scope of the present invention. The present invention should only be limited by the following claims and their legal equivalents.

DETAILED DESCRIPTION OF THE INVENTION

Figure 1:
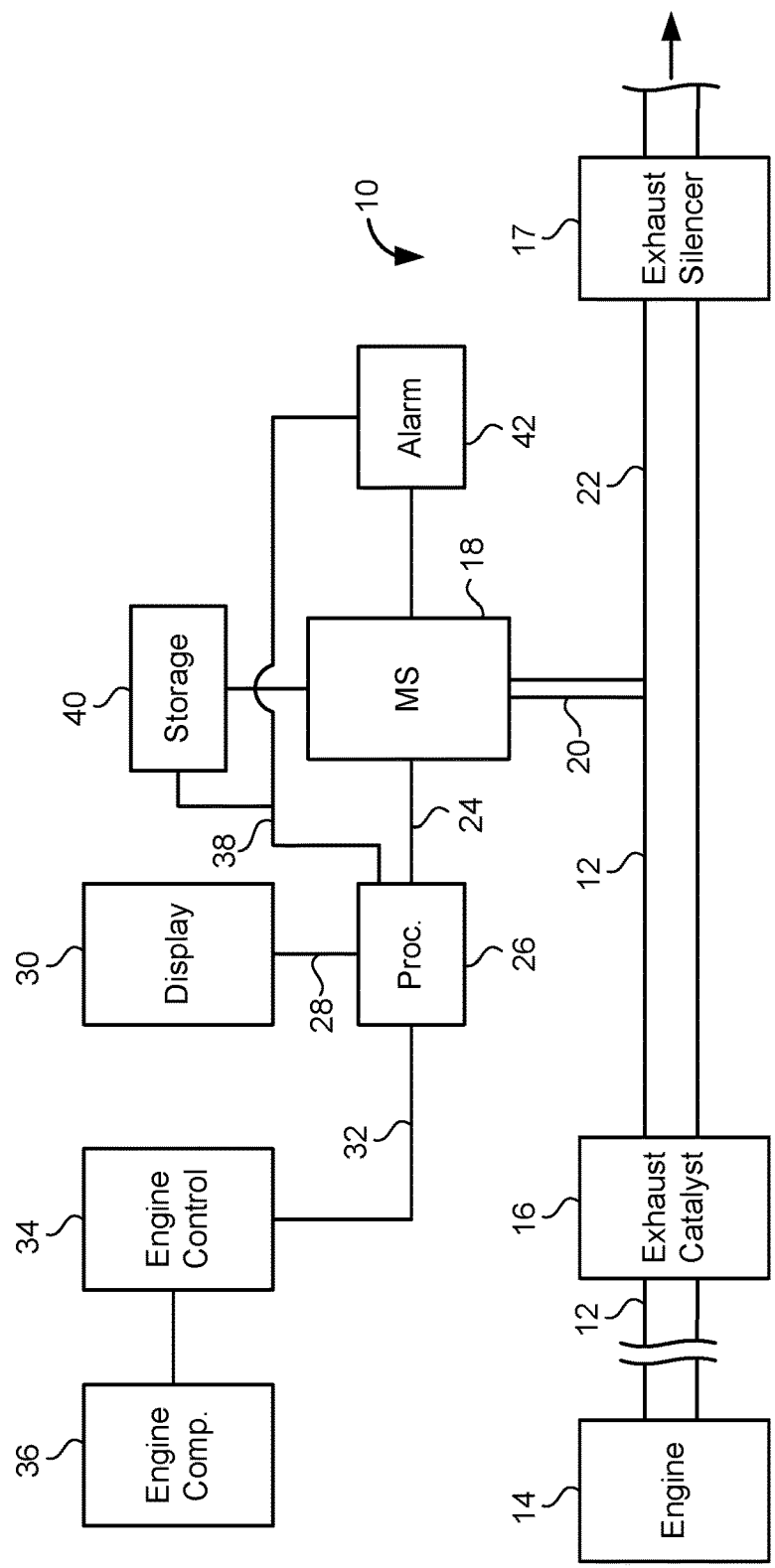
FIG. 1 is a block diagram showing the system and method of the present invention.

Referring to FIG. 1, there shown the system 10 in accordance with the teachings of the present invention. The system 10 is applied to an exhaust line 12 associated with an internal combustion engine and, in particular, with a natural gas-powered engine. In particular, the exhaust line 12 is connected at one end to the cylinder exhaust of engine 14. The cylinder exhaust can be in the nature of a manifold or separate pipes extending to each of the cylinders. The exhaust line 12 extends from the cylinder exhaust of engine 14 to the catalyst 16. The exhaust then flows along exhaust line 12 from the exhaust catalyst 16 to the exhaust silencer 17. Ultimately, the exhaust will flow from exhaust silencer 17 to the atmosphere. In particular, in FIG. 1, it can be seen that the system 10 is cooperative with the exhaust line 12 in an area between the exhaust catalyst 14 and the exhaust silencer 17.

In FIG. 1, there is a methane sensor 18 that is connected by a line 20 so as to communicate with the interior flow path 22 of the exhaust line 12. The line 20 can be in the nature of a stainless steel tube that is suitably plumbed to the exhaust line 12. Suitable fittings can be provided so that this communication can be achieved. During operation of the engine, the cylinder exhaust 14 will pass exhaust gases through the exhaust line 12. A portion of the exhaust gases will flow through the line 20 to the methane sensor 18. The methane sensor 18 is particularly designed to sense the concentrations of methane within the exhaust gases flowing through the flow pathway 22 within the exhaust line 12.

The methane sensor 18 is connected by a line 24 to a processor 26. The processor 26 has a plurality of outputs. One output 28 of the processor 26 is directed to a display 30. The display 30 can be mounted where appropriate. The display 30 will provide positive feedback to the operator or mechanics of the level of methane concentrations within the exhaust gas. The display 30 can also be in the nature of lights that are mounted to the housing of the methane sensor 18 (as will be described hereinafter).

The processor 26 also includes a line 32 that is directed to an engine controller 34. The engine controller 34 is cooperative with the engine components 36. As such, the engine can be particularly adapted relative to the methane concentrations that are passing through the exhaust line 12. For example, if excess methane emissions are occurring, then the engine controller 34 can suitably shut down the engine components 36 until the problem is rectified. In other circumstances, the engine controller 34 may reduce the rpms of the engine components 36 so as to achieve the proper amount of methane emissions. In other circumstances, the engine controller 34 can direct more power to the spark plugs that are firing the gas within the cylinder. This can achieve a more complete combustion of the exhaust gases and reduce the amount of methane concentrations.

The processor 26 is further connected to a line 38 that is directed to a memory or storage 40. As such, as the methane sensor 18 continuously samples and monitors the methane concentrations within the flow pathway 22 of exhaust line 12, the level of concentrations can be continuously stored within the storage 40. As such, if regulatory authorities desired to see the history of the operation of the engine, the storage 40 can provide suitable data to the regulatory authorities. This can further protect the operator against fines or other sanctions. The processor 26 is further connected to an alarm 42. Alarm 42 can be in the nature of lights or sound. An alarm can sound or light up when excess methane is passing through the flow pathway 22 of the exhaust line 12. As a result, the operator can immediately take steps so as to reduce this excess amount of methane concentrations. If networked properly, the user is able to monitor the engine methane concentration from anywhere in the world. The alarms can be configured to trip at any methane concentration deemed necessary by the user.

FIG. 1 further shows that the methane sensor 18 can be directly connected to the storage 40 and also can be directly connected to the alarm 42. As such, the present invention contemplates the isolated use of the methane sensor 18 as opposed to the incorporation of the processor 26. The alarm 42 can be directly mounted onto the housing of the methane sensor 18. Similarly, the storage can be in the nature of a circuit board that is connected to the methane sensor 18.

Figure 2:
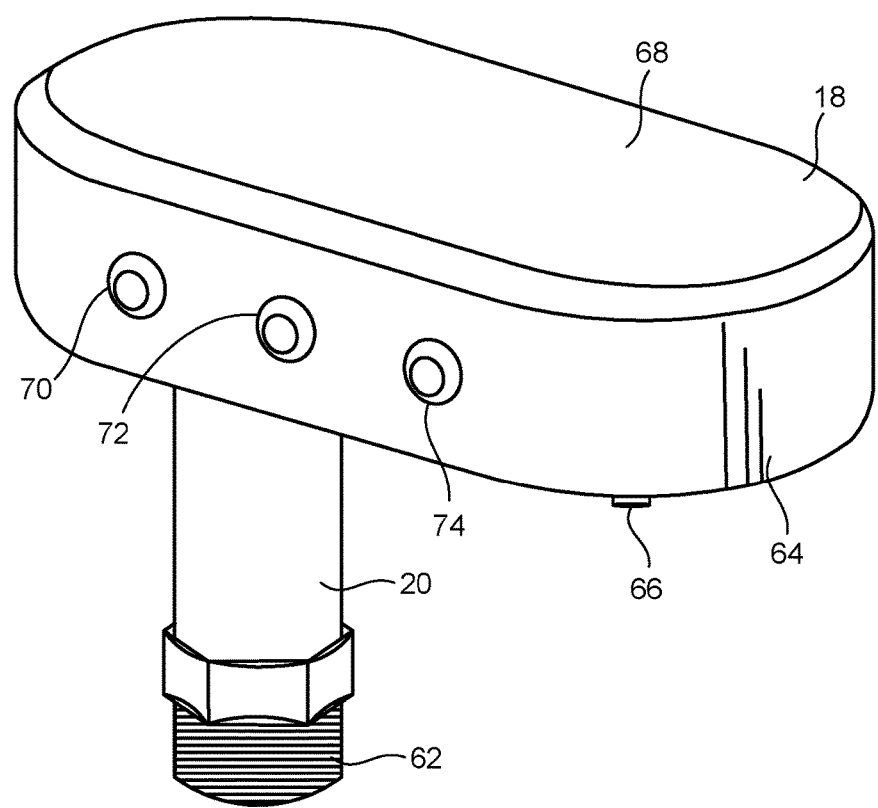
FIG. 2 is a perspective view showing the device in accordance with the teachings of the present invention.

FIG. 2 is illustrates a simple form of the methane sensor 18. This simple form of the methane sensor 18 includes line 20 extending therefrom. Line 20 can be in the nature of a stainless steel tube that communicates with the interior of the methane sensor 18. The line 20 includes a threaded connector 62 at a lower end thereof. The threaded connector 62 can connect with another line that is plumbed to the engine exhaust.

In FIG. 2, the methane sensor 18 includes its methane sensing components within a housing 64. Additionally, the housing 64 includes a mounting plate 66 at a lower end thereof. Alternatively, the housing 64 can utilize a mounting plate located at the top 68 of the housing 64. A plurality of warning lights 70, 72 and 74 are positioned on the housing 64. The lights 70, 72 and 74 can be indicative of the proper operation of the methane sensor 18, indicative of normal operating conditions and also indicative of excess methane. Additionally, within the concept of the present invention, the housing 64 can integrate an alarm thereon so that an audio output can be emitted in the event of detection of excess methane.

Figure 3:
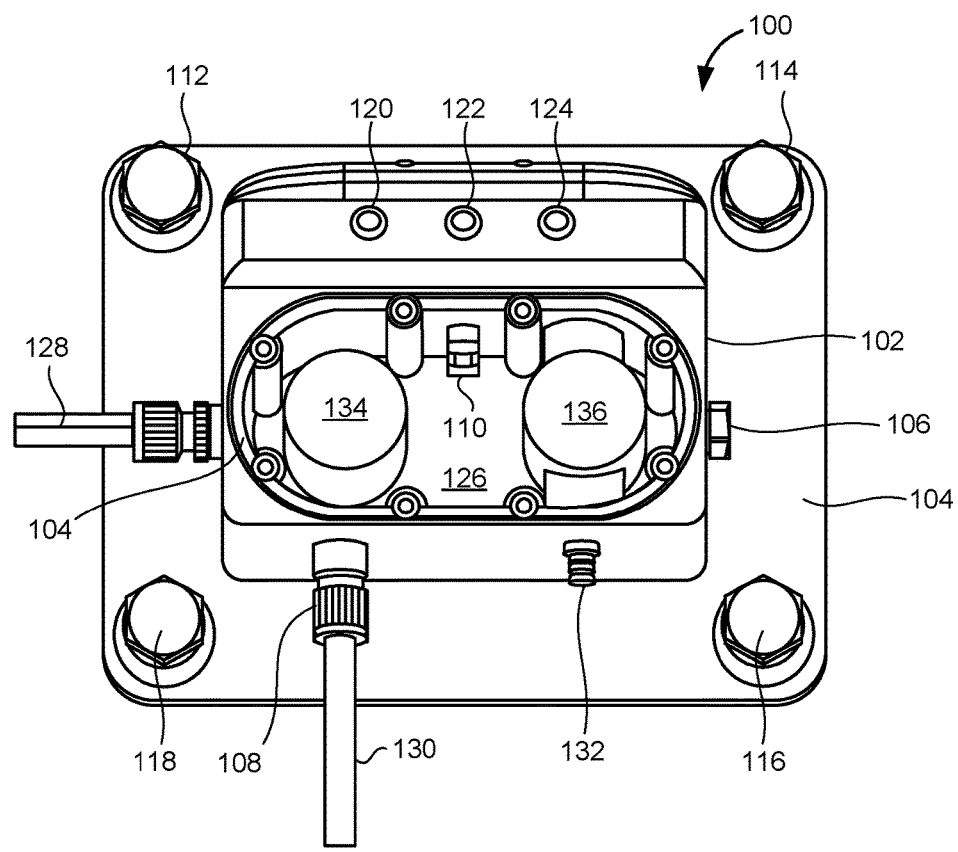
FIG. 3 is in internal view of the methane sensing apparatus in accordance with the first embodiment of the present invention.

Referring to FIG. 3, there is shown the methane sensing apparatus 100 in accordance with a first embodiment of the present invention. The methane sensing apparatus 100 includes a housing 102 that is supported upon a skid 104. The housing 102 includes a first inlet 104, a second inlet 106, and an outlet 108. A catalytic methane sensor 110 is positioned at an upper portion of the housing 102. A plurality of bolts 112, 114, 116 and 118 extend through the skid 104 so as to allow the skid 104 to be mounted to the skid of the engine or directly to the engine. Mounting bolts 112, 114, 116 and 118 can also include shock mounts so that vibration is effectively isolated from the housing 102.

The housing 102 includes indicator lights 120, 122 and 124 on an outer surface thereof. These indicator lights 120, 122 and 124 can be indicative of the level of methane concentration within the interior 126 of the housing. The light 120 can be a green light, light 122 can be a yellow light, and light 124 can be a red light. The green light represents an acceptable level of methane concentration. The yellow light represents an elevated level of methane concentration. The red light represents a level of methane concentration that is unacceptable and represents a mechanical problem with the engine. Each of these lights 120, 122 and 124 can be easily and humanly perceivably observable from an exterior of the housing 102.

The inlet 104 is connected to a line 128. Line 128 is plumbed to the exhaust line of the engine in one location. The inlet 166 can also have a line extending therefrom. This line would be plumbed to the exhaust line of the engine in a different location from that of line 128. As such, a first portion of the exhaust gas would flow into the interior 126 through the inlet 104 from the line and another portion of the exhaust gas would flow into the interior 126 through the line connected to the inlet 106. This achieves more accurate sampling since the sampling occurs in two different locations along a single exhaust line or inputs from separate exhaust banks. The outlet 108 includes another line 130 connected thereto. Line 130 can also be plumbed to the exhaust line. Importantly, outlet 108 allows any water to be removed from the interior 126 of housing 102. Water vapor is always present in the exhaust stream of a natural gas-fueled engine and rapidly condenses to form droplets as the engine exhaust cools. As such, any water that would enter the interior 126 should be removed before it encounters the catalytic methane sensor 110. It can be seen that the outlet 108 is located at a level lower than that of the inlet 104 and the inlet 106. The outlet 108 is also located at a level lower than that of the catalytic methane sensor 110. As such, by action of gravity, any water that enters the interior 126 of the housing 102 will flow downwardly so as to be discharged outwardly of the housing 102 through the outlet 108 and through the line 130.

Another outlet 132 can also communicate with the interior 126 of the housing 102. This also can be plumbed to the exhaust line or simply an opening so as to allow water to drip outwardly from the housing 102.

The methane sensing apparatus 100 of the present invention is particularly unique in that the system utilizes baffles 134 and 136 within the interior 126 of the housing 102. Baffle 134 is placed adjacent to the inlet 104 and above the outlet 108. Baffle 126 is positioned adjacent to the inlet 106 and above the outlet 132. As a portion of the exhaust gases flows through the inlet 104, they encounter the curved or geometric surface of the baffle 134. As such, this portion of the exhaust gas will have to flow around the baffle 134. This causes the water droplets to separate from the exhaust gas. Ultimately, these water droplets will be released from the baffle 134 by action of gravity and be discharged from the housing 102 through the outlet 108. Since the catalytic methane sensor 110 is located above the level of the inlet 104 and the outlet 108, the action of gravity will prevent these water droplets from any sort of damaging contact with the catalytic sensor 110. The baffle 136 has a similar configuration to the baffle 134 and can operate in conjunction with the portion of the exhaust gases that flow through the inlet 106.

In normal use, the portion of the exhaust gas will enter the interior 126 of the housing 102 on a continuous basis. This exhaust gas will continually circulate since it is been released through the outlets 108 and 132. As such, the exhaust gas continuously fills the housing 102 and is constantly entering and exiting the housing. This allows the catalytic methane sensor 110 to continuously monitor the methane concentration that is present in the engine exhaust.

The methane sensing apparatus 100 of FIG. 3 is a catalytic methane sensor. This catalytic methane sensor is small in physical size and offers a high degree of durability. It also presents a high level of durability and reliability in the presence of a corrosive gas, such as hydrogen sulfide. The methane sensing apparatus is relatively small with an overall size approximately seven inches by nine inches.

Figure 4:
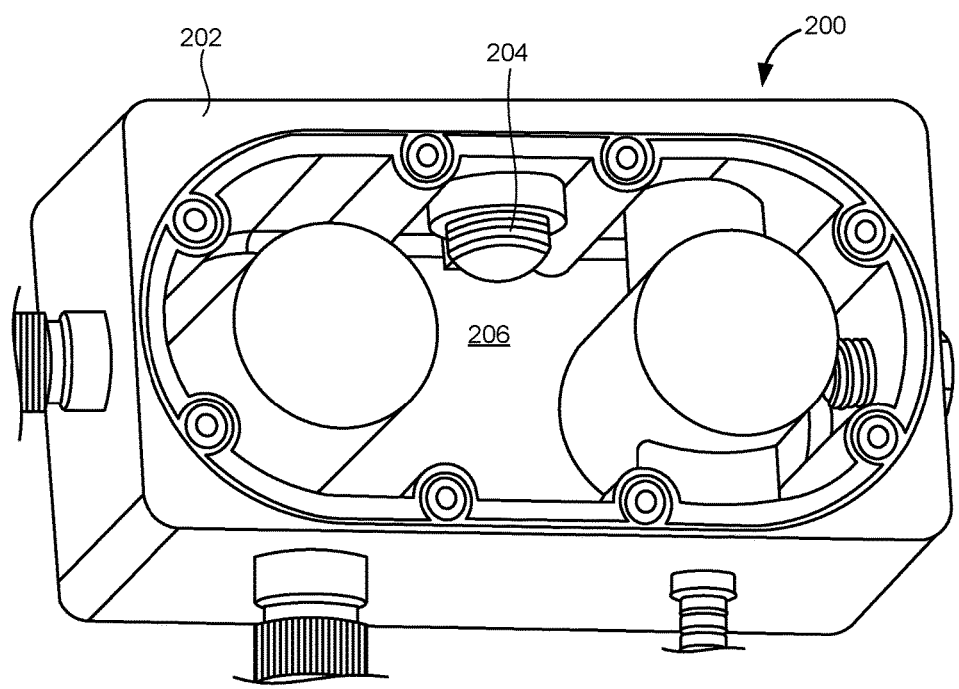
FIG. 4 is an internal view of the methane sensing apparatus in accordance with a second embodiment of the present invention.

FIG. 4 shows a second embodiment of the methane sensing apparatus 200 of the present invention. The methane sensing apparatus 200 includes a housing 202 having a similar configuration to that of the housing of methane sensing apparatus 100 of FIG. 3. However, in FIG. 4, an electrochemical cell 204 is used instead of the catalytic methane sensor of methane sensing apparatus 100. The electrochemical cell 204 is very accurate when operated within limitations defined by the manufacturer. It is often less than ideal for most oil and gas applications because of its fragile operating characteristics. This electrochemical cell 204 extends into the interior 206 of the housing 202 so as to contact the exhaust gas that is passed into the interior 206.

Figure 5:
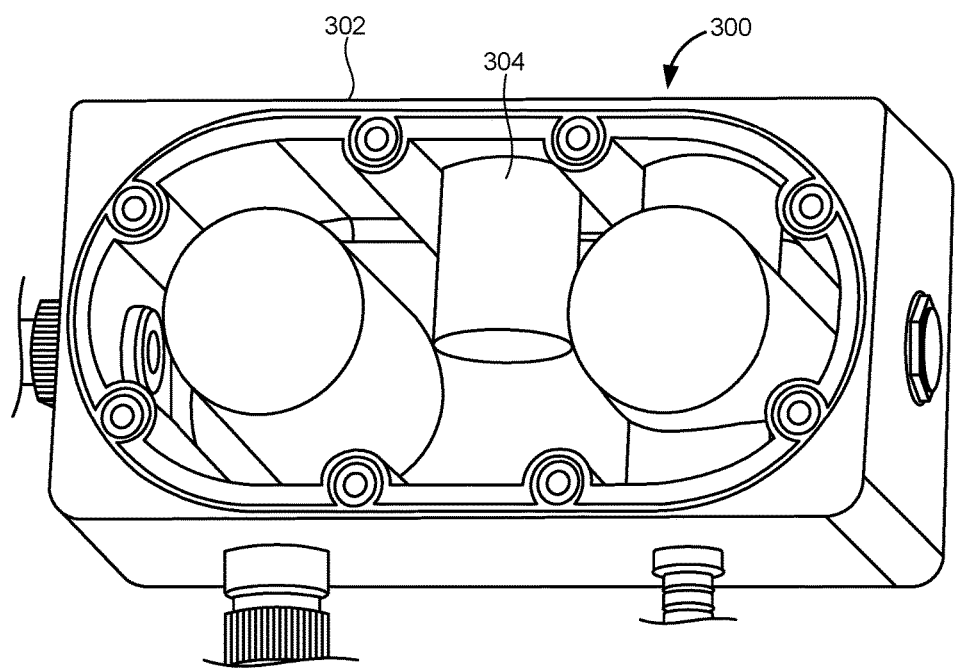
FIG. 5 is an internal view of the methane sensing apparatus in accordance with a third embodiment of the present invention.

FIG. 5 shows a third embodiment of the methane sensing apparatus 300 of the present invention. Methane sensing apparatus 300 has a housing 302 with an infrared methane sensor 304 extending downwardly from the upper wall of the housing 302. This infrared methane sensor is ideally suited for the application in the present invention, except for cost. The infrared methane sensor 304 will accurately measure the methane concentration from 0% to 10% or 100,000 ppm. Although the infrared methane sensor 300 has superior performance, the cost of the methane sensing apparatus 300 would be greater than that of the previous embodiments.

The foregoing disclosure and description of the invention is illustrative and explanatory thereof. Various changes in the details of the illustrated construction can be made is the scope of the present claims without departing from the true spirit of the invention. The present claims should only be limited by the following claims and their legal equivalents.

I claim:

1. A process for measuring methane emissions by an internal combustion engine, the process comprising:
   positioning a methane sensor at an upper location within a housing, a portion of the gas in an exhaust line of the internal combustion engine entering said by said methane sensor, said housing being connected to the exhaust line of the internal combustion engine;
   forming a baffle within said housing in a location such that the portion of the gas encounters said baffle prior to measurement by said methane sensor such that only gas flows through said housing to said methane sensor;
   connecting the methane sensor to the exhaust line of the internal combustion engine such that the portion of a gas in said exhaust line can enter said housing;
   operating the internal combustion engine so as to produce the exhaust;
   measuring a methane content of the gas with said methane sensor from the portion of the gas from the exhaust line;
   producing an output from said measurement sensor corresponding to the methane concentration;
   separating water from the portion of the gas by said baffle prior to the measurement by said methane sensor; and
   discharging the water outwardly from an interior of said housing.

2. A process for measuring methane emissions by an internal combustion engine, the process comprising:
   positioning a methane sensor at an upper location within a housing, a portion of the gas in an exhaust line of the internal combustion engine entering said housing prior to measurement by said methane sensor, said housing being connected to the exhaust line of the internal combustion engine;
   forming a baffle within said housing in a location such that the portion of the gas encounters said baffle prior to measurement by said methane sensor such that only gas flows through said housing to said methane sensor comprising;
   connecting the methane sensor to the exhaust line of the internal combustion engine such that the portion of a gas in said exhaust line can enter said housing;
   operating the internal combustion engine so as to produce the exhaust;
   measuring a methane content of the gas with said methane sensor from the portion of the gas from the exhaust line; and
   producing an output from said measurement sensor corresponding to the methane concentration, the step of connecting comprising extending the line from an inlet of said housing to the exhaust line, the step of forming the baffle comprising:
   positioning said baffle within said housing adjacent to said inlet; and
   forming an outlet of said housing in a location below said baffle.

* * * * *